(12) United States Patent
Barlow et al.

(10) Patent No.: US 8,251,926 B2
(45) Date of Patent: Aug. 28, 2012

(54) PACIFIER SYSTEM FOR STUDYING AND STIMULATING THE HUMAN OROFACIAL SYSTEM

(75) Inventors: Steven M. Barlow, Lawrence, KS (US); Donald S. Finan, Boulder, CO (US)

(73) Assignee: University of Kansas, Lawrence, KS (US)

( * ) Notice: Subject to any disclaimer, the term of this patent is extended or adjusted under 35 U.S.C. 154(b) by 1566 days.

(21) Appl. No.: 11/209,029

(22) Filed: Aug. 22, 2005

(65) Prior Publication Data
US 2006/0074354 A1    Apr. 6, 2006

Related U.S. Application Data

(60) Provisional application No. 60/605,607, filed on Aug. 30, 2004.

(51) Int. Cl.
*A61B 5/103* (2006.01)
*A61B 5/117* (2006.01)
*A61J 17/00* (2006.01)

(52) U.S. Cl. ........ 600/590; 600/587; 600/595; 606/234; 606/236

(58) Field of Classification Search .......... 600/587, 600/589, 590; 606/234, 235, 236
See application file for complete search history.

(56) References Cited

U.S. PATENT DOCUMENTS

| | | | |
|---|---|---|---|
| 3,790,016 A | 2/1974 | Kron | |
| 4,232,687 A | 11/1980 | Anderson-Shanklin | |
| 5,693,073 A | 12/1997 | Glick et al. | |
| 5,830,235 A | 11/1998 | Standley et al. | |
| 6,033,367 A | 3/2000 | Goldfield et al. | |
| 6,120,528 A | 9/2000 | Link et al. | |
| 6,264,678 B1 | 7/2001 | Landers | |
| 6,468,294 B2 | 10/2002 | Griffith | |
| 6,591,140 B2 * | 7/2003 | Strome et al. | 607/61 |
| 6,966,904 B2 | 11/2005 | Ruth et al. | |
| 2001/0047189 A1 | 11/2001 | Griffith | |
| 2004/0039358 A1 | 2/2004 | Rollin et al. | |
| 2006/0079814 A1 | 4/2006 | Barlow et al. | |

FOREIGN PATENT DOCUMENTS

FR    2729843    8/1996
(Continued)

OTHER PUBLICATIONS

"International Preliminary Report on Patentability (including the International Search Report and Written Opinion) for PCT Application No. PCT/US2005/031169, mailed Dec. 21, 2006", 11 pgs.

(Continued)

*Primary Examiner* — Max Hindenburg
*Assistant Examiner* — Adam Eiseman
(74) *Attorney, Agent, or Firm* — Schwegman, Lundberg & Woessner, P.A.

(57) ABSTRACT

The present subject matter is suited for evaluating biomechanics and electrophysiology of an infant's orofacial system during sucking. The present subject matter includes at least one orofacial sensor and a processor. In various examples, the present subject matter additionally includes one or a combination of: a pacifier having a baglet, a receiver assembly, a stimulation device, a memory, a display, and data acquisition and analysis software. Advantageously, the present subject may non-invasively sample and analyze suck and may stimulate nerve endings in the face of an infant.

35 Claims, 7 Drawing Sheets

FOREIGN PATENT DOCUMENTS

| WO | WO-0009006 | 2/2000 |
|---|---|---|
| WO | WO-2006/026623 A2 | 3/2006 |
| WO | WO-2006/033801 A1 | 3/2006 |
| WO | WO-2008127733 | 10/2008 |

OTHER PUBLICATIONS

"International Search Report for corresponding PCT Application No. PCT/US2005/030869,mailed Apr. 25, 2006", 7 pgs.

"Written Opinion for corresponding PCT Application No. PCT/US2005/030869 mailed Apr. 14, 2006", 9 pgs.

Andreatta, R. D., et al., "Low-level Static Lip Force Control Does Not Alter Vibrotactile Detection Thresholds in the Human Orofacial System", *Experimental Brain Research*, 151, (2003), 548-552.

Andreatta, R. D., et al., "Movement-Related Modulation of Vibrotactile Detection Thresholds in the Human Orofacial System", *Experimental Brain Research*, 149, (2003),75-82.

Barlow, S. M., et al., "Actifier II: The Dynamics of Sensorimotor Integration During Suck in Neonates and Infants", *12th Biennial Conference on Speech Motor Control*, Albuquerque, NM, (Mar. 20, 2004), 19 pgs.

Barlow, S. M., et al., "Chapter 9—Sensorimotor Entrainment of Respiratory and Orofacial Systems in Humans", *In: Speech Motor Control in Normal and Disordered Speech*, B. Maassen, et al., Editors, Oxford University Press, 16 pgs.

Barlow, S. M., et al., "Mechanically Evoked Peroral Reflexes in Infants", *Brain Research*, 599 (1), (1992), 158-160.

Barlow, S, M., et al., "Mechanosensory Modulation of Trigeminofacial Pathways During Speech", *Society for Neuroscience*, 2820, (2002), 1 pg.

Barlow, S. M., "Modulation of Mechanically Evoked Perioral Reflexes During Active Force", *Brain Research*, 565(2), (1991), 330-336.

Barlow, S. M., et al., "Physiological Studies of the Human Vocal Tract Across the Lifespan", *4th Annual Willard R. Zemlin Award Lecture in Speech Science Session*. 1138., ASHA National Convention, Chicage, IL, (Nov. 14, 2003), 56 pgs.

Finan, D. S., et al., "Dynamic Loading of the Developing Human Respiratory System: A New Method", 135-29, ASHA National Convention, Chicago, IL, (Nov. 13, 2003), 3 pgs.

Finan, D. S., et al., "The Actifier: A Device for Neurophysiological Studies of Orofacial Control in Human Infants", *Journal of Speech and Hearing Research*, vol. 39, (Aug. 1996), 833-838.

Seibel, L., et al., "Actifier II: The Dynamics of Non-Nutritive Suck in Neonates and Infants", *12th Biennial Conference on Speech Motor Control*, Albuquerque, NM, (Mar. 20, 2004), 8 pgs.

"U.S. Appl. No. 11/209,177 Non-Final Office Action mailed on Dec. 8, 2008", 6 pgs.

"U.S. Appl. No. 11/209,177, Final Office Action mailed Jun. 26, 2009", 9 pgs.

"U.S. Appl. No. 11/209,177, Response Filed Mar. 9, 2009 to Non-Final Office Action mailed Dec. 8, 2008.", 13 pgs.

200580036193.5, "Chinese Application Serial No. 200580036193.5, Office Action mailed Mar. 10, 2009", 6 Pages.

Lau, Chantal, "Oral Feeding in the Preterm", *NeoReviews*, 7 (1), (Jan. 2006), e19-e27.

Pickler, Rita H, et al., "Effects of non-nutritive sucking on nutritive sucking, breathing, and behavior during bottle feedings of preterm infants", *Adv Neonatal Care*, 4(4), (Aug. 4, 2004), 226-34.

"U.S. Appl. No. 11/209,177, Examiner Interview Summary mailed Feb. 25, 2009", 2 pgs.

"U.S. Appl. No. 11/209,177, Examiner Interview Summary mailed Nov. 19, 2009", 3 pgs.

"U.S. Appl. No. 11/209,177, Response filed Nov. 27, 2009 to Final Office Action mailed Jun. 26, 2009", 16 pgs.

"U.S. Appl. No. 11/209,177, Non Final Office Action mailed Apr. 14, 2011", 8 pgs.

"Chinese Application Serial No. 200580036192.0, Office Action mailed Oct. 12, 2010", 6 pgs.

"Chinese Application Serial No. 200580036192.0, Office Action Response Filed Feb. 28, 2011", 12 pgs.

"Chinese Application Serial No. 200580036193.5, Office Action mailed Apr. 26, 2011", 11 pgs.

"European Application Serial No. 05814103.7, Office Action Response Filed Apr. 14, 2011", 32 pgs.

"European Application Serial No. 05797922.1, Examination Notification mailed Mar. 25, 2011", 7 Pgs.

Barlow, S. M, et al., "Mechanically evoked perioral reflexes in infants", Brain Res., 599(1), (Dec. 18, 1992), 158-60.

Finan, D. S, et al., "The Actifier: A Device for Neurophysiological Studies of Orofacial Control in Human Infants", Journal of Speech and Hearing Research, 39, (Aug. 1996), 833-838.

"European Application Serial No. 05814103.7, Office Action mailed Oct. 5, 2010", 4 Pgs.

"U.S. Appl. No. 11/209,177 , Response filed Oct. 13, 2011 to Non Final Office Action mailed Apr. 14, 2011", 11 pgs.

"Chinese Application Serial No. 200580036193.5, Office Action Response filed Sep. 13, 2011", 9 pgs.

"European Application Serial No. 05797922.1, Office Action Response filed Aug. 31, 2011", 13 pgs.

"International Application Serial No. PCT/US2005/030869, International Preliminary Report on Patentability mailed Jan. 26, 2007", 13 pgs.

"International Application Serial No. PCT/US2005/031169, Written Opinion mailed Feb. 1, 2006", 6 pgs.

\* cited by examiner

PRESSURE WAVE FORM

FIGURE 6A

PERIOD HISTOGRAM

PACIFIER SYSTEM FOR STUDYING AND STIMULATING THE HUMAN OROFACIAL SYSTEM

CLAIM OF BENEFIT OF PRIOR-FILED APPLICATION

This patent application claims the benefit of U.S. Provisional Application Ser. No. 60/605,607, entitled "Pacifier System for Studying and Stimulating the Human Orofacial System," filed on Aug. 30, 2004, under 35 U.S.C. §119(e), which is hereby incorporated by reference in its entirety.

CROSS-REFERENCE TO RELATED APPLICATION

This application is related to U.S. Patent Application, entitled "Pacifier System for Stimulating and Entraining the Human Orofacial System," filed even date herewith Ser. No. 11/209177, which is hereby incorporated by reference in its entirety.

STATEMENT AS TO RIGHTS TO INVENTIONS MADE UNDER FEDERALLY SPONSORED RESEARCH AND DEVELOPMENT

The subject matter discussed in this patent application was funded in part by United States Grant No. RO1-DC03311-01 from the National Institute of Health (NIH). The government may have certain rights to the subject matter discussed below.

TECHNICAL FIELD

This patent application pertains generally to system and methods for evaluating animals, and more particularly, to systems and method for studying and stimulating a human orofacial system.

BACKGROUND

The developing brain of a typical human fetus adds thousands of neurons per minute. During fetal development and at birth, neural cells link to specific neurological functions. It follows that a newborn infant's brain develops neuron-neurological function connections in light of post birth experiences.

In premature birth, the premature infant loses opportunities for safe neurological development in utero. This loss can be compounded by medical complications associated with premature birth, such as strokes or hemorrhages. Further, medical complications often are treated with painful procedures which correlate with impairment in neurological development. Each of these stresses can affect a premature infant's ability to suck, swallow, or breathe on their own. Such impairments can affect the development of intelligence and speech.

This problem affects several hundred thousand babies annually in the United States. Many of these babies suffer with a partially developed nervous system, respiratory system, and/or other anatomy. Fortunately, since the brain continues to develop throughout life, damaged neurological networks can be overcome by early detection and treatment. However, many of these neurological impairments and developmental disabilities are not discovered using available diagnostic tools. What are needed are new tools to identify problems earlier.

SUMMARY

Various embodiments of the present subject matter include a system for testing suck capabilities and the mechanically evoked trigeminal-facial reflex in premature babies, newborns, and infants. In various embodiments, the system includes at least one orofacial sensor and at least one processor.

Various embodiments of the present subject matter apparatus and methods for analyzing subject's suck using a force-feedback sensing approach.

In one embodiment, the present subject matter provides a system for use with a subject having a mouth, the system comprising: a baglet, adapted for non-nutritive sucking on by the subject; a plurality of orofacial sensors, adapted to sense at least one non-nutritive suck signal and at least one facial musculature signal, the plurality of orofacial sensors including a plurality of electrodes configured to sense the at least one facial musculature signal; a processor, adapted to receive the at least one non-nutritive suck signal and the at least one facial musculature signal; and a stimulus device configured to apply a mechanical stimulus on tissue of the subject outside of the subject's mouth, the stimulus device using at least one sensor for operating the stimulus device under force-feedback, such that the stimulus device is programmed to follow movement of at least a portion of the tissue outside of the subject's mouth to impart stimulus delivery, wherein the processor is configured to automatically compute a non-nutritive suck profile indication using one or both of: the at least one non-nutritive suck signal and the at least one facial musculature signal, and to compute a suck deficiency indication using, at least in part, the non-nutritive suck profile indication and a predetermined suck profile, and the stimulus device provides the stimulus based, at least in part, on the suck deficiency indication.

In one embodiment, the present subject matter provides a system for evaluating an orofacial system of a subject having a mouth, the system comprising: a plurality of orofacial sensors including a plurality of electrodes configured to sense at least one facial musculature signal from the subject; a processor, adapted to receive each facial musculature signal; and a stimulation device, coupled to the processor and configured to impart a stimulus to the orofacial system of the subject adjacent to the subject's mouth, the stimulation device operated using a force-feedback configuration, such that the stimulation device is programmed to follow movement of at least a portion of the orofacial system adjacent to the subject's mouth to impart stimulus delivery, wherein the processor is adapted to compute a non-nutritive suck profile indication using the at least one facial musculature signal and to compute a suck deficiency indication using, at least in part, the non-nutritive suck profile indication and a predetermined suck profile.

In one embodiment, the present subject matter provides a system for evaluating an orofacial system of a subject having a mouth, the system including a baglet, adapted for non-nutritive sucking on by the subject; a plurality of orofacial sensors, adapted to sense at least one non-nutritive suck signal and at least one facial musculature signal; a processor, adapted to receive each non-nutritive suck signal and each facial musculature signal; a stimulation device, coupled to the processor and adapted to impart a stimulus to the orofacial system of the subject near the subject's mouth, the stimulation device operated in a force-feedback configuration, such that the stimulation device is programmed to follow movement of at least a portion of the orofacial system adjacent to the subject's mouth to provide stimulus delivery; and a display device, coupled to the processor, wherein at least one orofacial sensor comprises a plurality of electrodes, and wherein the processor is adapted to compute a non-nutritive suck profile indication using one or both of: the at least one non-nutritive suck signal and the at least one facial musculature signal and to compute a suck deficiency indication using, at least in part, the non-nutritive suck profile indication and a predetermined suck profile.

In one embodiment, the present subject matter provides a method comprising: sensing a non-nutritive suck signal from a subject; sensing electrical potential information of the subject's perioral musculature; computing a non-nutritive suck profile indication using one or both of: the non-nutritive suck signal and the electrical potential information; comparing the non-nutritive suck profile indication to a predetermined suck profile; and providing a stimulus to the subject's tissue adjacent to the subject's mouth, the stimulus based, at least in part, on comparing the non-nutritive suck profile indication to the predetermined suck profile, the stimulus applied using a force-feedback approach programmed to follow movement of at least a portion of the tissue adjacent to the subject's mouth to provide stimulus delivery.

In one embodiment, the present subject matter provides a method including coupling a plurality of orofacial sensors to a processor; coupling a stimulation device to the processor, the stimulation device configured to produce a physical force on a subject's orofacial system adjacent to the subject's mouth and to operate under force-feedback, such that the stimulation device is programmed to follow movement of the subject's orofacial system adjacent to the subject's mouth to impart effective stimulus delivery; and mounting the plurality of orofacial sensors, the processor, and the stimulation device in a device adapted to interface with orofacial tissue, wherein at least one orofacial sensor is adapted to sense a non-nutritive suck signal, wherein at least one orofacial sensor is adapted to sense electrical potential information from orofacial tissue, and wherein the processor is adapted to compute a suck profile indication using one or both of: the non-nutritive suck signal and the electrical potential information, and to compute a suck deficiency indication using, at least in part, the non-nutritive suck profile indication and a predetermined suck profile.

The present subject matter in various embodiments may allow for the non-invasive, objective, and rapid performance of an electrophysiologic assessment of the trigeminal-facial function and suck biomechanics in infants at risk for neurological impairments and developmental disabilities.

This Summary is an overview of some of the teachings of the present application and not intended to be an exclusive or exhaustive treatment of the present subject matter. Further details about the present subject matter are found in the detailed description and appended claims. The following detailed description and drawings that form a part thereof provide some examples of the present subject matter and are not to be taken in a limiting or exclusive sense. The scope of the present invention is defined by the appended claims and their legal equivalents.

The present subject matter may allow for the non-invasive, objective, and rapid performance of an electrophysiologic assessment of the trigeminal-facial function and suck biomechanics in infants at risk for neurological impairments and developmental disabilities.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present application.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Figure 1:
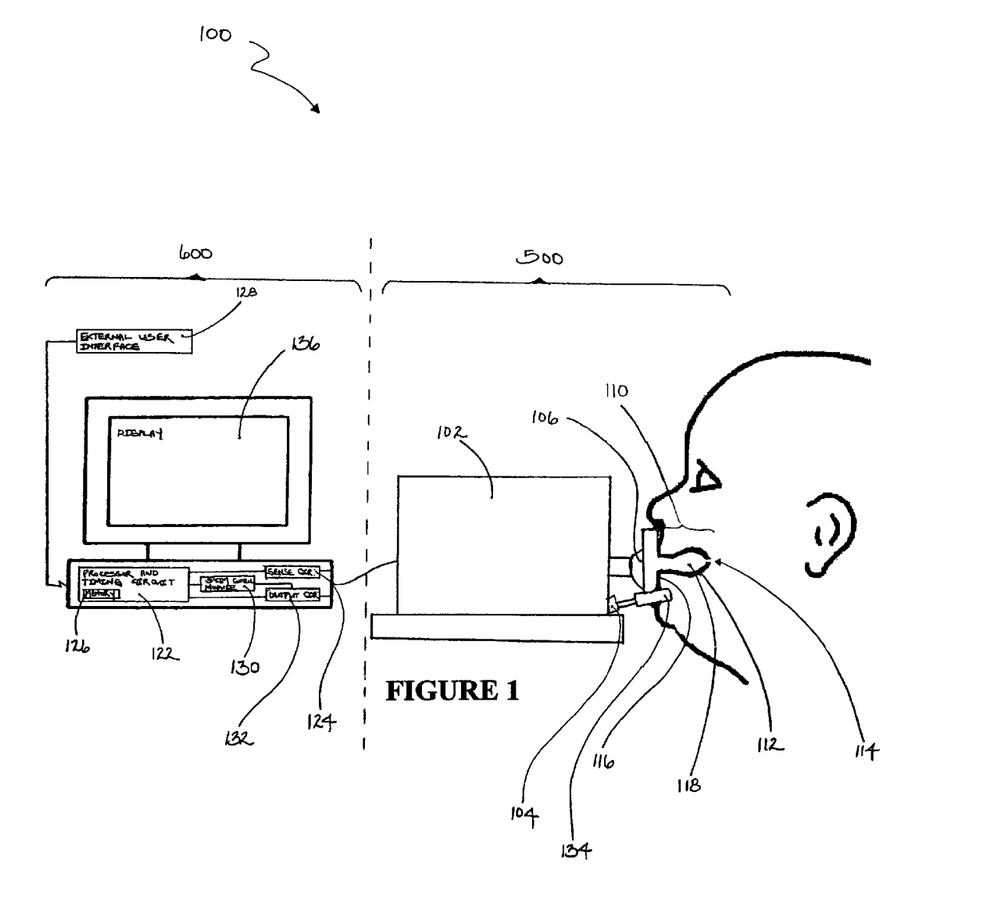
FIG. 1 is a partial side view, having a cut-away, and illustrating a system having a first portion 500 and a second portion 600 for studying a patient, according to one embodiment of the present subject matter.

FIG. 1 is a partial side view, having a cut-away, and illustrating a system having a first portion 500 and a second portion 600 for interacting with a patient, according to one embodiment of the present subject matter. In various embodiments, the system is adapted for studying the biomechanics and electrophysiology of an infant's orofacial system during non-nutritive sucking. The present subject matter, however, additionally is adapted for study of other biomechanics and electrophysiology. In various embodiments, a system 100 includes a housing 102 to accommodate, among other things, a motor 104 and a receiver assembly 106. Attached to the motor 104 may be a stimulus applicator 134, in various embodiments. In some examples, an adjustable size relation may exist between the stimulus applicator 134 and the receiver assembly 106. For example, some embodiments use larger stimulus applicators 134 paired with smaller receiver assemblies 106. Additional embodiments pair smaller stimulus applicators 134 with larger receiver assemblies 106.

In various examples, the receiver assembly 106 is instrumented with an orofacial sensor, such as a suck sensor, to sense a suck signal from an infant. In various examples, the receiver assembly 106 is adapted for detachable coupling of a pacifier 110 via a ring-groove configuration. In one example, the pacifier 110 used in system 100 is a medical grade silicon pacifier, such as a SOOTHIE pacifier. SOOTHIE is a registered trademark of Children's Medical Ventures, Inc., which is incorporated in Delaware. Other pacifier makes and models additionally fall within the scope of the present subject matter. Various embodiments use pacifiers available in at least three sizes: micro-premature infants, premature infants, and term infants.

In some examples, the pacifier 110 includes a baglet 112 having a baglet opening 114 and a baglet base 116. In some example, the pacifier 110 further includes a baglet cavity 118. In some examples, the suck sensor is pneumatically coupled to the baglet opening 114 to sense the suck signal from the infant when the pacifier is inserted into the infant's mouth. Various examples of suck sensors are discussed herein. In various examples, the system 100 includes one or more orofacial sensors, such as facial musculature sensors, to sense one or more facial musculature signals from the infant. In some examples, the one or more sensors each include an electrode that is positioned at or near the baglet base 116. Various examples of facial musculature sensors are discussed herein.

Various examples of the present subject matter include a processor 122, which may co-exist with a timing circuit. In one example, the processor 122 is electrically coupled to the suck sensor 108 to receive the suck signal, and is further electrically coupled to each facial musculature sensor 120 to receive the one or more facial musculature signals. In some examples, both the suck signal and the facial musculature signals are first received by a sense detection circuit 124 before being communicated to the processor 122. In various examples, the processor 122 uses the suck signal and the facial musculature signals to execute instructions to compute a suck profile indication. In some examples, the processor 122 uses only the facial musculature signals to execute instructions to compute the suck profile indication.

The suck profile indication provides a summary of the infant's suck capabilities, which may be compared with a predetermined suck profile, in various embodiments. In some embodiments, sensed suck and facial musculature signals are included in the suck profile indication. Various embodiments provide a suck profile indication of one or more similarly-aged neurologically intact infants. For example, some embodiments provide a suck profile indication for infants not suffering from neurological impairments or developmental disabilities.

In addition to computing the suck profile indication, the processor 122, in various examples, also executes instructions to compute a suck deficiency indication. In some examples, the suck deficiency indication is computed using the suck profile indication and one or more predetermined suck profiles. In various examples, the one or more predetermined suck profiles are stored in a memory 126 of the processor 122. In some examples, the one or more predetermined suck profiles are communicated to the memory 126 by way of an external user interface 128. The external user interface 128 provides an input device for a user and is communicatively coupled to the processor 122, in various embodiments.

In various examples, the processor 122 is electrically coupled to a stimulus control module 130. The stimulus control module 130, in various embodiments, is configured to adjust or initiate a stimulus based on the suck deficiency indication computed by the processor 122. Some embodiments include a punctuate mechanical stimulus. The stimulus control module 130 adjusts or initiates a stimulus by generating a stimulus control signal. In various embodiments, stimulus control module 130 communicates a stimulus control signal to an output circuit 132. Upon receiving the stimulus control signal, the output circuit 132 may in turn activate the motor 104, in various examples. In various examples, the motor 104 receives electrical communication from the output circuit 132 and transduces such communication into a mechanical action. In one example, the motor 104 is a linear motor which transposes the electrical communication to one or more linear displacements. In some examples, a stimulus applicator 134 is mechanically coupled to the motor 104 and imports the mechanical action to the infant's face. One type of mechanical action is displacement, but others additionally fall within the present scope.

In various embodiments, the motor 104 includes at least one stimulation device sensor to sense information related to the stimulus applicator's 134 impact against the subject. In various embodiments, the sensor measures impact against the subject's face. Additional sensors sense the stimulus applicator's position relative to the housing 102. The sense circuit 124, in various embodiments, is capable of receiving sense information from the at least one stimulation device sensor. Various embodiments provide sense information to the processor 122. The processor 122 is adapted to analyze the sense information and compare it to available stored data. Various embodiments use this sense information to improve patient satisfaction, by reducing harmful force subjected to the face. In one embodiment, this is accomplished by the processor 122 through computation of a signal directing movement of motor 104. In some examples, such signal is communicated to the motor 104 by way of the output circuit 132.

Various embodiments include one or more displays 136, to project data sensed by a suck sensor, data sensed by the facial musculature sensors 120, and/or the at least one stimulation device sensor. In various embodiments, the display additionally projects data analyzed by the processor 122. In various embodiments, the display projects data entered via the external user interface 128. In some embodiments, data displayed on one or more displays 136 is visible in real time.

In various examples, the memory 126 is configured to one or more predetermined suck profiles. Memory 126, in various examples, is additionally configured to store a history of one or a combination of the suck signal, the facial musculature signals, the suck profile indication, the suck deficiency indication, the stimulus control signal, the force information (e.g., force signal), and/or the displacement information (e.g., displacement signal).

Figure 2:
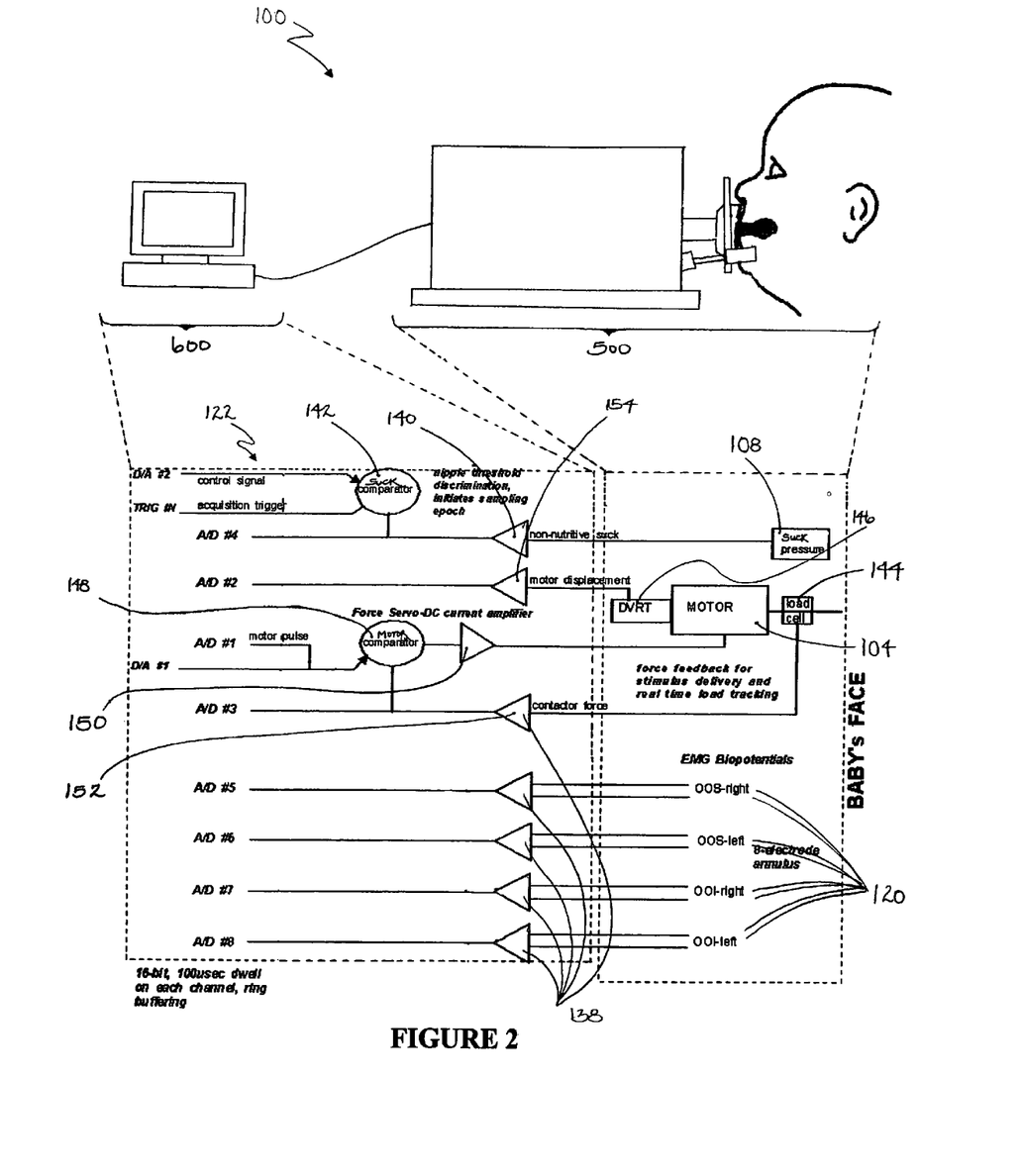
FIG. 2 is a schematic diagram illustrating portions of a system as constructed in accordance with at least one embodiment of the present subject matter.

FIG. 2 is a schematic diagram illustrating a patient measurement system 100 having a first portion 500 and a second portion 600, according to one embodiment of the present subject matter. In various embodiments, the system 100 is capable of studying the biomechanics and electrophysiology of an infant's orofacial system during non-nutritive sucking. In various embodiments, the system includes an orofacial sensor, such as a suck sensor 108; a motor 104; numerous stimulation device sensors 144, 146; numerous orofacial sensors, such as facial musculature sensors 120; and/or a processor 122. In some examples, system 100 is powered by plugging an integrated cord into an electrical outlet. In another example, the system 100 is powered by one or more batteries which may provide for greater mobility. Other power sources may also be employed without departing from the scope of the present subject matter.

In one example, the suck sensor 108 senses a suck signal from an infant and communicates the signal to the electrically coupled processor 122. In one example, the suck sensor 108 is pneumatically coupled to a pacifier 110 having a baglet 112. In various embodiments the suck sensor 108 generates a suck signal when the baglet 112 is inserted into the infant's mouth and sucked on by the infant. In various embodiments, the suck signal is amplified by a suck amplifier 140 to provide an amplified suck signal. The amplified suck signal may be used by a suck comparator 142 and converted from an analog signal to a digital signal. The suck comparator 142 is adapted to compare the amplified suck signal sensed from the infant to one or more predetermined suck profiles. As discussed above, the one or more predetermined suck profiles are based on observations from similarly-aged infants who are neurologically intact. In various examples, the one or more predetermined suck profiles are stored in a memory 126. After comparing the amplified suck signal to one or more predetermined suck profiles, the suck comparator 142 can compute a suck deficiency indication.

Based on the suck deficiency indication, in various embodiments, the processor 122 may execute instructions to compute a stimulus control signal to activate the motor 104, which may be adapted to stimulate the infant. In various examples, the stimulus control signal is sent to a motor comparator 148. In additional embodiments, the stimulus control signal is amplified by a motor amplifier 150 to provide an amplified stimulus control signal. The amplified stimulus control signal, in some examples, moves motor 104, which causes movement of a stimulus applicator relative to an infant's face. In various embodiments, movement depends on signals provided to the processor 122 by at least one stimulation device sensor. In one example, the motor 104 is a linear motor coupled to a stimulus probe. In an additional example, the stimulus probe acts as the stimulus applicator.

In some embodiments, the motor is adapted to allow for up to 8 mm of tracking displacement. In additional embodiments, the motor is adapted to allow for up to 15 mm of tracking displacement. Other tracking displacements are additionally within the scope of the present subject matter. Varying embodiments of the present subject matter allow for tracking displacement under forced feedback conditions.

In some examples of the present subject matter, the motor 104 may be integrated with numerous stimulation device sensors, such as a load cell 144 and a differential variable reluctance transducer (DVRT) 146. The load cell 144 provides force information (e.g., via a force signal) of the motor 104 by transposing force into an electrical signal, in various embodiments. In one example, the force signal is amplified by a force amplifier 152 and is used by the motor comparator 148 and converted from an analog signal to a digital signal. The motor comparator 148 compares the amplified force signal to a predetermined, preprogrammed force threshold to ensure the stimulus applicator 134 does not harm the infant's face, in various embodiments. In some examples, the DVRT 146 provides position information of the motor 104 by transposing motor displacement into an electrical signal. In one embodiment, position information is based on a displacement signal. In one example, the displacement signal is amplified by a displacement amplifier 154 and converted from an analog signal to a digital signal.

The instrumentation of the load cell 144 and the DVRT 146 with the motor 104 allows the stimulus applicator 134 (FIG. 1) to operate under force-feedback for stimulus delivery and real time force tracking, in various embodiments. Force-feedback signifies that the stimulation device may be programmed to closely follow the infant's face to accurately import one or more stimuli to the same. In one example, the stimulus applicator may follow the infant's face in real time. Such real time tracking allows the stimulus applicator to import accurate, effective stimulus delivery whether or not the infant's face is moving.

In one example, numerous facial musculature sensors 120 each include an electrode. In one example, the electrodes non-invasively sense and provide to the electrically coupled processor 122 one or more facial musculature signals. In one example, eight electrodes are divided into four channels of signals. The facial musculature signals are amplified, in various embodiments, by numerous facial musculature sensor amplifiers 138 and are converted from analog signals to digital signals by way of one or more signal conditioners. In one example, the facial musculature signals are amplified by GRASS P511 Bioamplifiers, which are manufactured by Grass Telefactor, a division of AstroMed of 600 East Greenwich Avenue, West Warwick, R.I. 02893. In one example, the facial musculature signals are converted from analog to digital signals by a 16-bit front end analog-to-digital card manufactured by National Instruments, Inc., of 11500 N Mopac Expressway, Austin, Tex. 78759-3504. Other amplifiers and signal conditioners are also possible without departing from the scope of the present subject matter. As will be discussed in greater detail below, the facial musculature sensors 120 may be used to sense activity the infant's brain is sending to the infant's face during sucking.

In various embodiments, the processor 122 can be configured to store, in real time, a history of one or a combination of the suck signal, the facial musculature signals, the suck deficiency indication, the stimulus control signal, and/or the force and displacement signals. Further, in various examples, the processor 122 is programmed to analyze and display, in real time, one or a combination of the suck signal, the facial musculature signals, the suck deficiency indication, the stimulus control signal, and/or the force and displacement signals. The real time storing, analyzing, and displaying of data, which is present in various examples of the system 100, may be achieved by one or more software programs communicated to the processor 122, in various embodiments. In some examples, a first software program is used for data acquisition purposes while a second software program is used to analyze and display the data in real time. In some examples, a single software program is used for data acquisition, analysis, and/or display purposes.

In one example, a software program is capable of real time multi-channel data acquisition, waveform display, and analysis of an infant's sucks biomechanics. One example automatically calculates and displays, in histogram for, suck "burst" periods, suck amplitude, and suck pause periods. In various embodiments, one or more of these data are displayed in real time. Additionally, in various embodiments, the software program is capable of performing frequency domain analysis (e.g., Fourier transforms) of suck burst events. In one example, the software program acquires data in 30 second time periods, with the number of data collection periods only limited by the PC-system's hard drive resources. Time periods of other amounts are also within the scope of the present subject matter. The software program of this example is capable of simultaneously sampling facial musculature from the infant's perioral muscles, including bilateral sampling of orbicularis oris superior and orbicularis oris inferior skin sites.

In various embodiments, a software program is capable of real time multi-channel data acquisition and graphical display of one or a combination of: stimulus control signals, force signals, displacement signals, suck signals, and/or facial musculature signals. The multi-channel data acquisition of some embodiments includes 8 channels, 16-bit, 100 microsecond dwell acquisition. In various embodiments, a software program performs pre-trigger (e.g., 50 milliseconds) and post-trigger (e.g., 100 milliseconds) data acquisition to capture a reflex activation and modulation of the trigeminal-facial reflex response during non-nutritive suck of infants. The software program, in various embodiments, ensures that mechanical stimulation to the infant's face evokes the trigeminal-facial reflex. Additionally, in various embodiments, a software program controls the stimulation in both time and location respects according to a reference to the infant's suck cycle. In one example, the software program is capable of simultaneously sampling facial musculature from the infant's perioral muscles, including bilateral sampling of orbicularis oris superior and orbicularis oris inferior skin sites (e.g., the sphincter muscle around the mouth, forming much of the tissue of the lips). In further examples, the software program of this example is capable of performing digital signal processing including: demeaning, rectifying, integration, and/or signal averaging of facial musculature signals in reference to a mechanical stimulus event.

Figure 3A:
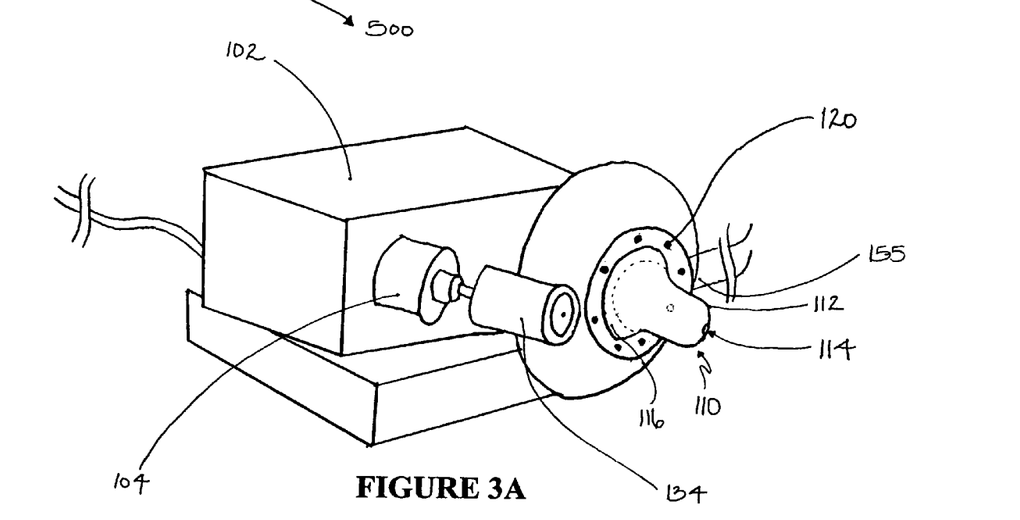
FIG. 3A is a perspective view illustrating a portion of a system as constructed in accordance with at least one embodiment of the present subject matter.

FIG. 3A is a perspective view of a first portion 500 of a system for monitoring a patient, according to one embodiment of the present subject matter. In various embodiments, the system is for studying biomechanics and electrophysiology of an infant's orofacial system during non-nutritive sucking. The present subject matter, however, additionally is adapted for study of other biomechanics and electrophysiology. In various embodiments, the first portion 500 of the system 100 includes a housing 102 to accommodate a motor 104 and a receiver assembly. Attached to the motor 104 may be a stimulus applicator 134, in various embodiments. In some examples, an adjustable size relation may exist between the stimulus applicator 134 and the receiver assembly. The receiver assembly, in various examples, is adapted for detachable coupling of a pacifier 110 via a ring-groove configuration. In one example, the pacifier 110 includes a baglet 112 having a baglet opening 114 and a baglet base 116. The baglet 112 is adapted for sucking on by an infant, in various embodiments.

The first portion 500 further includes one or more orofacial sensors, such as facial musculature sensors 120, in various embodiments. In some examples, each facial musculature sensor 120 may include an electrode. As discussed above, the facial musculature sensors 120 may be used to non-invasively sense and provide at least one facial musculature signal from the infant to a processor 122. The eight facial musculature sensors 120 illustrated each include an electrode, in various embodiments. In one example, the eight electrodes are located at the baglet base 116 and are arranged annularly to mate with a curvature of the infant's face. In one example, the eight electrodes may be 4 mm diameter discs, which are spaced 4.5 mm apart from one another. In another example, the electrodes aligning with the corners of the infant's mouth may include a 2 mm vertical offset. Such spacing and offset may allow each electrode to establish effective communication with the infant's face, and thus, may ensure accurate facial musculature signals are sensed, in various embodiments. In some examples, the facial musculature sensors 120 are electrically connected to a measurement system by a quick-connect connection 155 providing for rapid assembly and disassembly.

Mechanically coupled to the motor 104 is a stimulus applicator 134, in various embodiments. In some examples, the stimulus applicator 134 is a stimulus probe. In one such example, the stimulus probe is 10 mm in diameter and is coupled to a Luer fitting for quick release. Other probe diameters and fittings may also be utilized without departing from the scope of the present invention. In various examples, the motor 104 receives a stimulus control signal from a processor, which the motor 104 transposes into a mechanical action, such as a linear motion. In some examples, the linear motion is imported, by way of the stimulus probe, to the infant's orofacial system. In one such example, the infant receives a facial indentation of approximately 600-900 microns during approximately a 10 millisecond time period. In various examples, the onset and timing of this mechanical stimulation is triggered in conjunction with the slope and pressure of the infant's suck. As discussed above, the mechanical stimulus is activated when the measurement system senses a suck pressure signal from the infant which, when compared to one or more predetermined suck profiles, is found to exhibit deficient characteristics. In response, a processor may synthesize a stimulus control signal that activates the motor 104.

In various embodiments, by presenting a mechanical stimulus to the face of an infant, neuromuscular activity may be evoked via the trigeminal and facial cranial nerves. Specifically, when a stimulus is presented to the face of the infant, sensory nerve endings that are part of the trigeminal system may be activated. These are known as primary mechanosensory neurons. As a result, nerve fibers in the trigeminal system may be activated and enter the infant's brain stem where inter-neurons link the infant's sensory system to the infant's motor apparatus. Motor neurons have cell bodies in the infant's facial nucleus which "fire" (e.g., activate) upon receiving sensory signals from the sensory neurons. By using one or more orofacial sensors, such as facial musculature sensors 120, at least one facial musculature signal (e.g., electromyographic (EMG) signal) may be recorded by the measurement system, in various embodiments. The significance of stimulating neuromuscular activity and measuring the infant's response, according to various embodiments of the present subject matter, is that such acts provide a strong developmental and diagnostic measurement of the infant's sucking capabilities. Additionally, various embodiments provide measurements which are quantitative, objective, and repeatable.

In some examples, the first portion 500 of the measurement system is adapted to be hand-held by a user. In additional embodiments, first portion 500 is adapted to be mountable to an external device. Other holding means that allow the measurement system 100, or associated subcomponents, to sense one or a combination of: at least one suck signal and at least one facial musculature signal and further import a stimulus to the infant are also within the scope of the present subject matter.

Figure 3B:
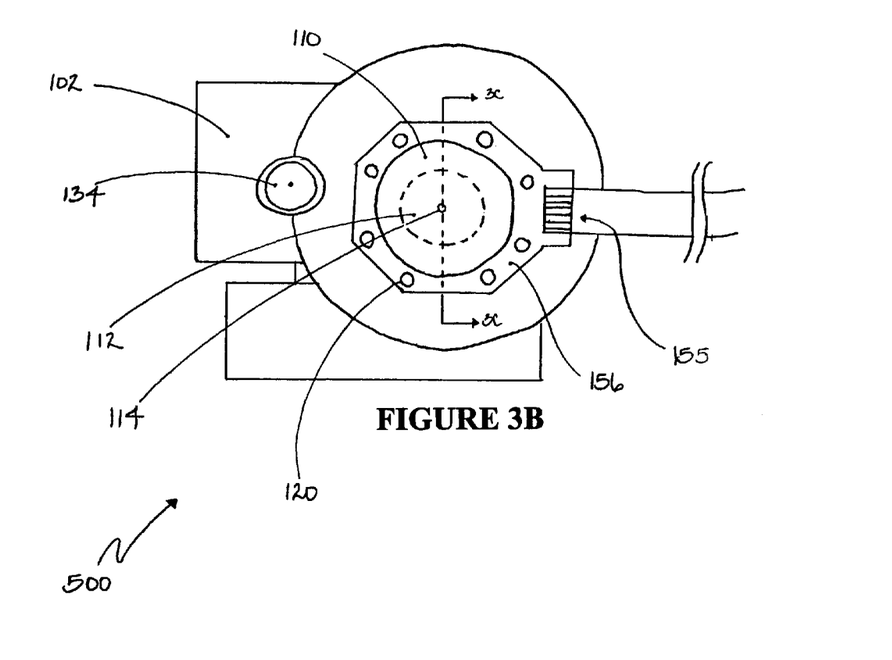
FIG. 3B is a frontal view illustrating the portion of a system illustrated in FIG. 3A.

FIG. 3B is a frontal view of the illustration of FIG. 3A. In various embodiments, the illustration demonstrates a tool capable of studying the biomechanics and electrophysiology of an infant's orofacial system during non-nutritive sucking. The present subject matter, however, additionally is adapted for study of other biomechanics and electrophysiology. First portion 500 includes a housing 102 to accommodate a motor 104 (FIG. 3A) and a receiver assembly, in various embodiments. In various examples, a pacifier 110 is detachably coupled to the receiver assembly. In one example, the pacifier 110 includes a baglet 112 having a baglet opening 114.

In one example, the first portion 500 includes one or more orofacial sensors, such as facial musculature sensors 120, and a stimulus applicator 134. In one example, eight facial musculature sensors 120, each including an electrode, are positioned annularly on an electrode PC-board 156. In some examples, the sensors are positioned on a circuit board for a PC. Various sensor configurations are shaped to mate with a curvature of an infant's face. In one example, the eight facial musculature sensors 120 are electrically connected to the measurement system by a quick-connect connection 155. In various examples, the stimulus applicator 134 may import a stimulus to the infant's face, such as a corner of the infant's mouth.

Figure 3C:
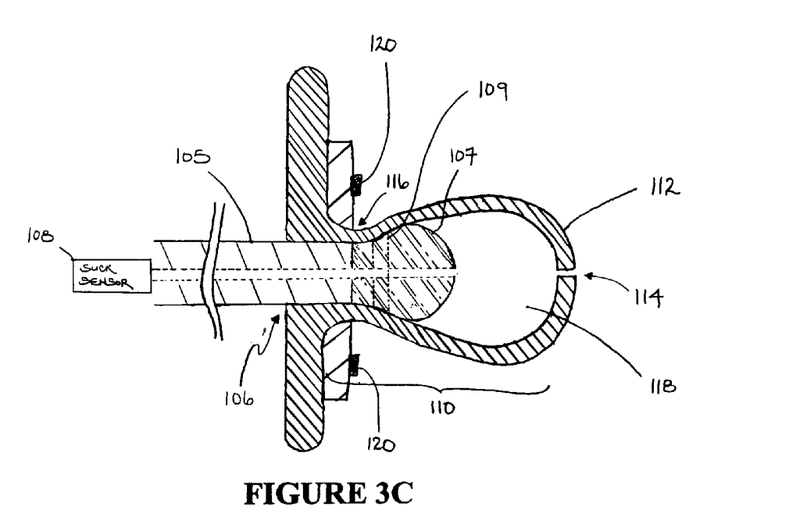
FIG. 3C is a cross-sectional view taken along line 3C-3C of FIG. 3B illustrating a portion of a system as constructed in accordance with at least one embodiment of the present subject matter.

FIG. 3C is a cross-sectional view taken along line 3C-3C of FIG. 3B. The illustration shows a receiver assembly 106, a pacifier 110, a suck sensor 108, and numerous orofacial sensors, such as facial musculature sensors 120, according to one embodiment of the present subject matter. It should be noted that other configurations within the scope of the present subject matter are adapted to use orofacial sensors besides suck sensor 108. The receiver assembly 106 may be adapted for a detachable coupling of the pacifier 110. Some embodiments of receiver assembly 106 include a ring-groove configuration. In one example, the detachable coupling is made possible via a receiver assembly 106 including a cannula 105 connecting a ball 107. In various embodiments, the cannula is stainless steel. Additional embodiments incorporate a ball which includes DELRIN materials. DELRIN is a registered trademark of the E.I. DuPont de Nemours and Company Corporation, 101 West 10$^{th}$ St., Wilmington, Del. 19898. The receiver assembly, in various examples, is ported for intra-(baglet) cavity 118 pressure transduction. In various embodiments, the ball 107 has a circumferential lip 109 which functions as a retainer for the pacifier 110 at or near a baglet base 116. In one example, pacifier 110 includes a baglet 112 having a baglet opening 114 and the baglet base 116. In one example, the pacifier 110 further includes a baglet cavity 118.

In various embodiments, the suck sensor 108 may sense a suck signal from an infant and communicate such signal to a processor. In some examples, the suck sensor 108 is pneumatically coupled to the baglet opening 114 to sense the suck signal. In some examples, the suck signal includes an indication of one or a combination of: a suck intensity, a suck duration, and a suck frequency. In one example, the suck sensor 108 is positioned within baglet cavity 118. In some examples, the suck sensor 108 is a pressure transducer, such as a pressure transducer manufactured by Honeywell International Inc., 101 Columbia Road, Morristown, N.J. 07962. In one example, the pressure transducer includes a bleed valve with Luer connections. Other pressure transducer makes and models may also be used without departing from the scope of the present subject matter. Similarly, other valves and connections may also be used without departing from the scope of the present subject matter.

Numerous facial musculature sensors 120 are adapted to non-invasively sense and communicate at least one facial musculature signal from the infant to a processor. In some examples, each facial musculature sensor 120 may include an electrode. In some examples, each of the numerous facial musculature sensors 120 is configured to sense at least one facial musculature signal. Additionally, in various embodiments, each of the facial musculature sensors 120 is configured to sense at least one suck signal. Various embodiments of the present subject matter do not include a suck sensor 108.

Figure 4:
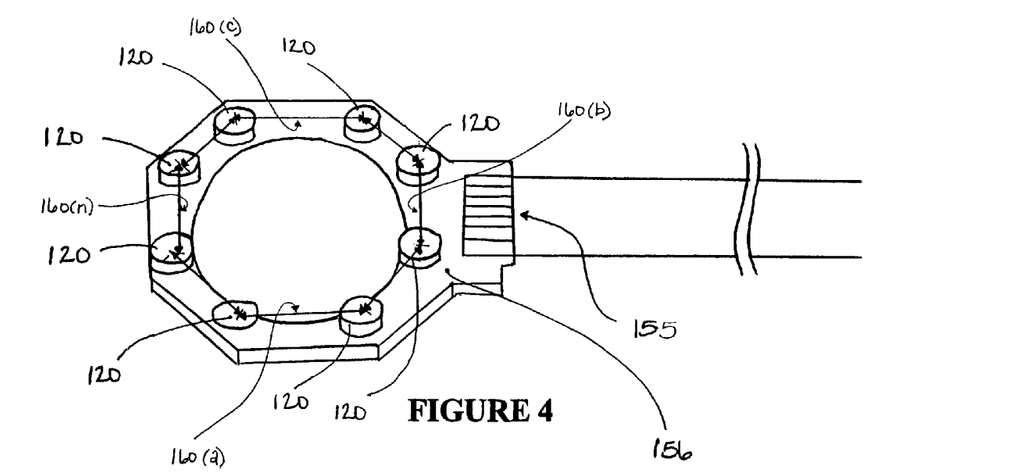
FIG. 4 is a perspective view illustrating an assembly of a system as constructed in accordance with at least one embodiment of the present subject matter.

FIG. 4 is a perspective view illustrating orofacial sensors, according to one embodiment of the present subject matter. Various embodiments of the present subject matter use one or more orofacial sensors, such as facial musculature sensors 120, capable of studying the electrophysiology of an infant's orofacial system during non-nutritive sucking. The present subject matter, however, additionally is adapted for study of other biomechanics and electrophysiology. In some examples, each facial musculature sensor 120 includes at least one electrode. In one example, the eight electrodes are arranged in four bipolar pairs providing four separate channels of information about an infant's orofacial system. For example, the spacing between any pair 160A, 160B, 160C, . . . , 160N is constant. Further, in one example, the eight electrodes are arranged annularly to mate with a curvature of an infant's face by way of maintaining spacing 160A, 160B, 160C, . . . , 160N. In one example, each such spacing measurement is 4.5 mm, while each electrode is a 4 mm diameter disc. In another example, the electrodes aligning with the corners of the infant's mouth may include a 2 mm vertical offset. In another example, at least one electrode is composed, at least in part, of gold. In yet another example, at least one electrode is composed, at least in part, of a material including silver/silver-chloride. Other electrode compositions may also be used without departing from the scope of the present subject matter. In a further example, each electrode is doped with CELLUVISC. CELLUVISC is a registered trademark of Allergan, Inc., Irvine, Calif. 92623. The present subject matter additionally includes other electrolyte solutions, to enhance the electrode's ability to sense EMG potentials from the infant's perioral musculature.

In various embodiments, a PC-board ring 156 accommodates the eight electrodes with spacing, as discussed above, to sense the infant's facial musculature signals. The spacing of the electrodes may be scalable to accommodate various face sizes of infants, in various embodiments. In one example, the PC-board ring 156 includes a quick-connect connection 155, such as a gold plated socket connection to provide communication between the facial musculature sensors 120 and a plurality of facial musculature sensor amplifiers.

Figure 5A:
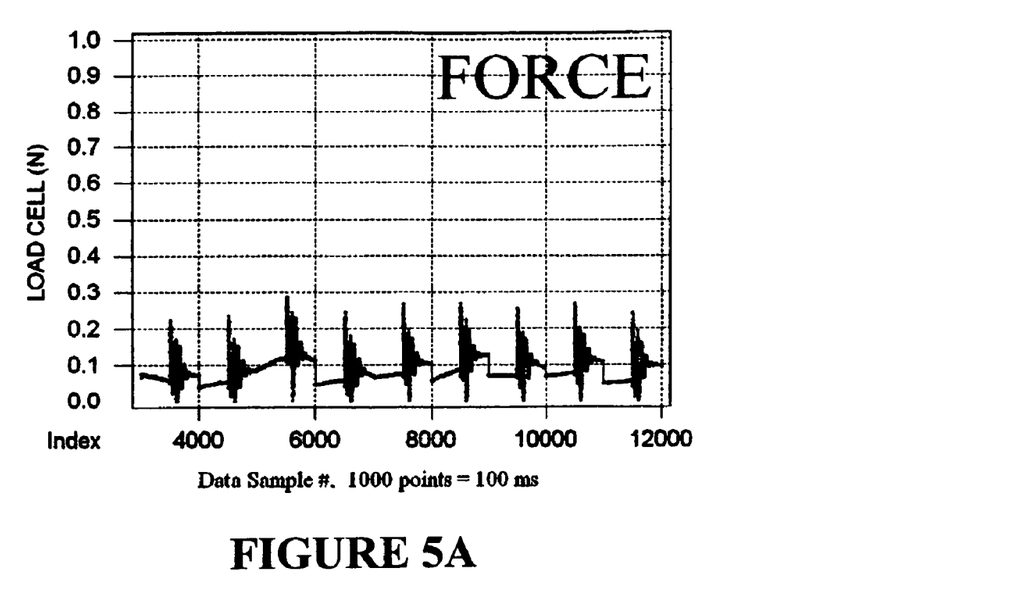
FIG. 5A is a graph illustrating performance of an element of a system as constructed in accordance with at least one embodiment of the present subject matter.
Figure 5B:
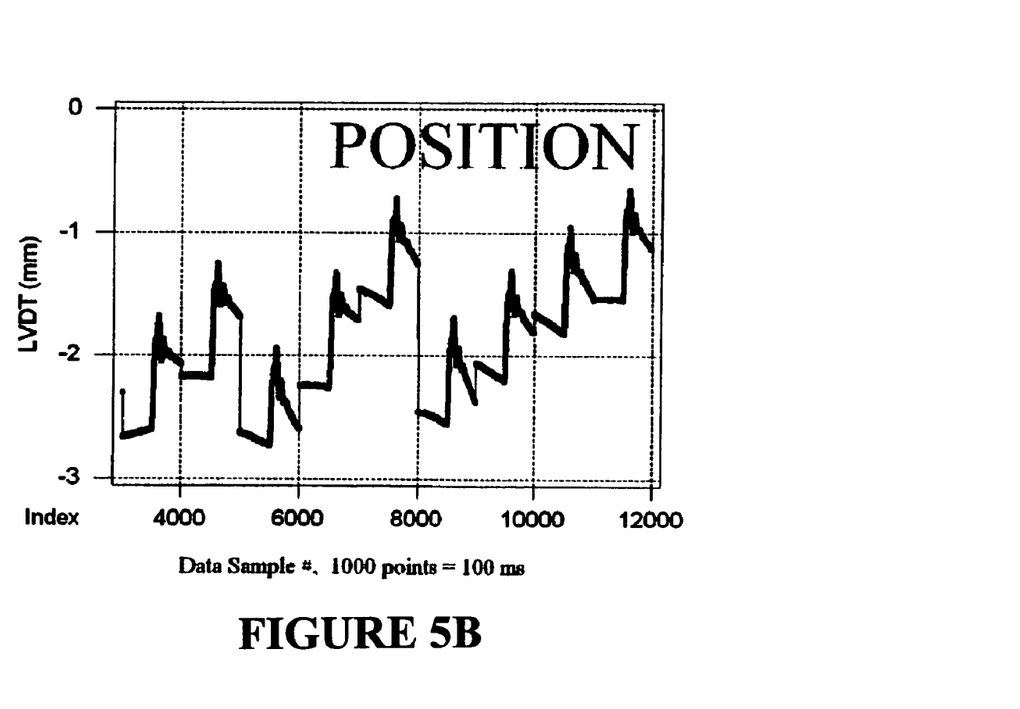
FIG. 5B is a graph illustrating performance of an element of a system as constructed in accordance with at least one embodiment of the present subject matter.

FIGS. 5A and 5B are graphs illustrating performance of a force-feedback feature of a motor during live non-nutritive sucking in premature infants. Specifically, FIGS. 5A and 5B graphically illustrate a force signal provided by a load cell and a displacement signal provided by a DVRT, respectively. As discussed above, in some examples, the motor may be integrated with at least one stimulation device sensor, such as a load cell or a DVRT. As further discussed above, the load cell provides force information in the form of a force signal of the motor 104, while the DVRT provides position information in the form of a displacement signal of the motor.

Figure 6A:
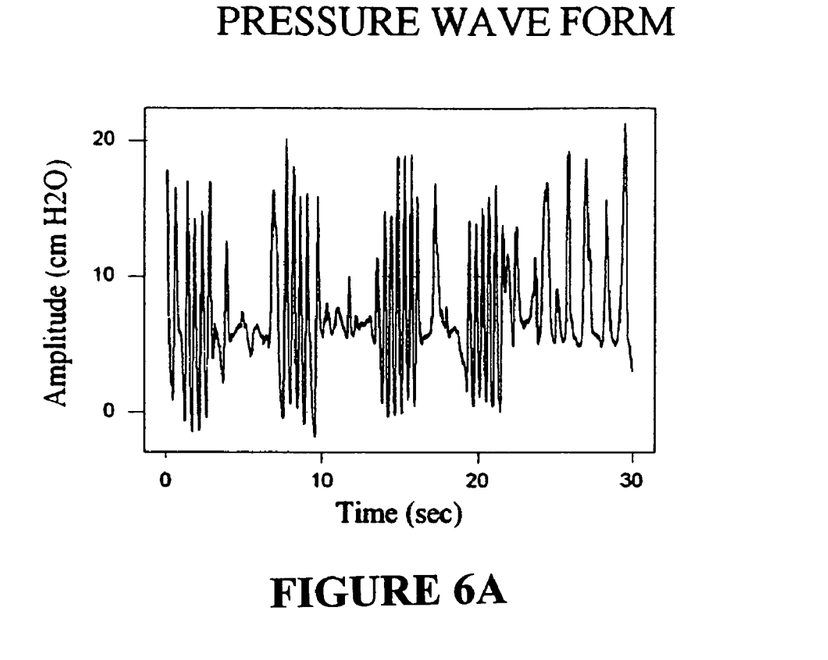
FIG. 6A is a graph illustrating data collected by a system as constructed in accordance with at least one embodiment of the present subject matter.
Figure 6B:
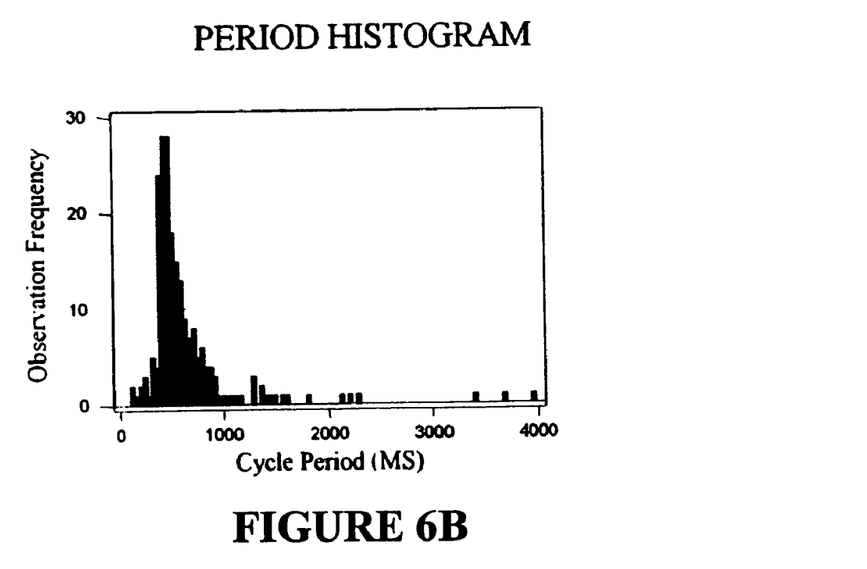
FIG. 6B is a graph illustrating data collected by a system as constructed in accordance with at least one embodiment of the present subject matter.

In some examples the suck signal may include information of one or a combination of: a suck intensity, a suck duration, and a suck frequency of an infant's suck. FIGS. 6A and 6B are graphs illustrating analysis which may be performed by the processor upon receiving a suck signal from an infant during non-nutritive suck. Specifically, FIG. 6A graphically illustrates one example of a real time pressure waveform indicative of the infant's suck intensity and suck duration. FIG. 6B graphically illustrates one example of a real time histogram indicative of the infant's suck frequency.

Figure 7:
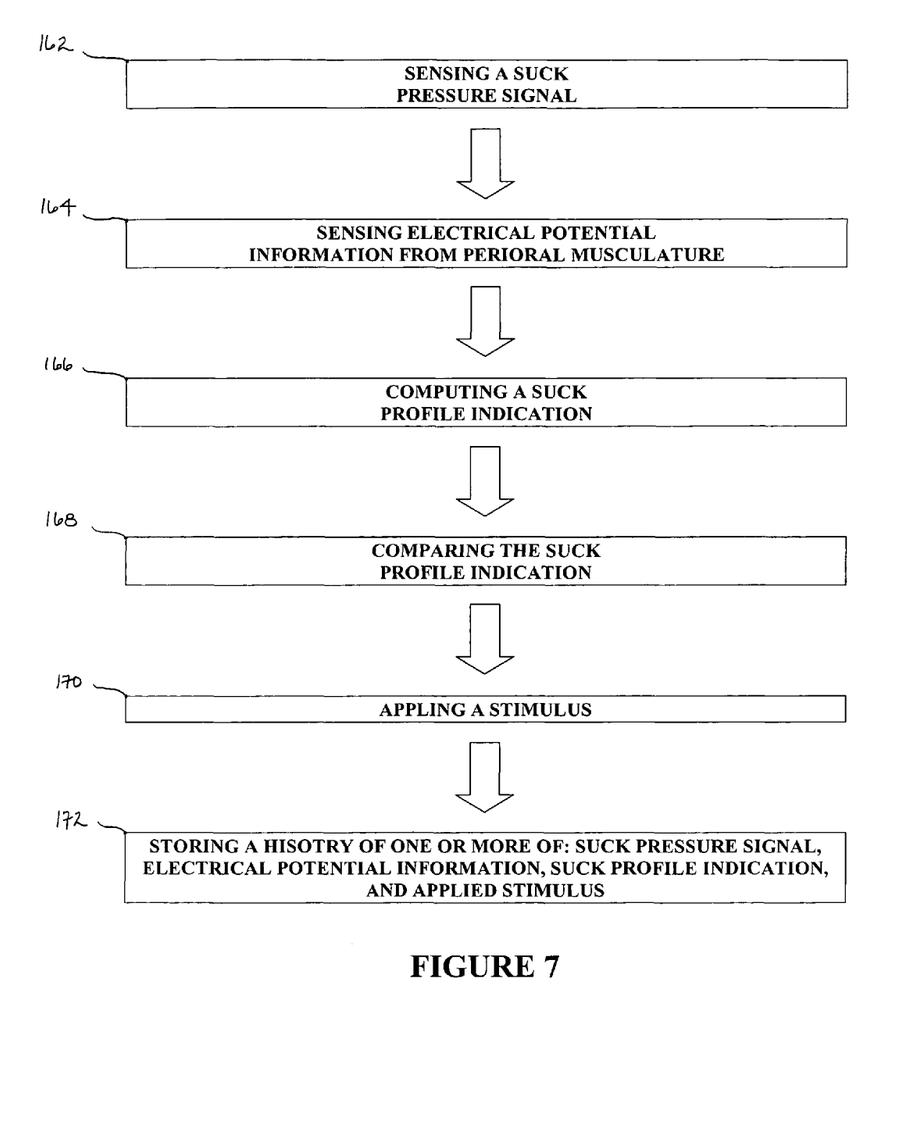
FIG. 7 is a flow chart illustrating a method as constructed in accordance with at least one embodiment of the present subject matter.

FIG. 7 illustrates one example of a method to study the biomechanics and electrophysiology of an infant's orofacial system during sucking. The method includes sensing a suck signal 162 from an infant, sensing electrical potential information from perioral musculature 164 of the infant, computing a suck profile indication 166 of the infant, and comparing the suck profile indication 168 to a predetermined suck profile. In various examples, sensing the suck signal 162 includes inserting a baglet of a pacifier into the infant's mouth, such as before a scheduled feeding (e.g., 15 minutes prior to scheduled feeding). In some examples, sensing the suck signal 162 includes sensing one or a combination of: a suck intensity, a suck duration, and a suck frequency associated with the infant's suck. In some examples, sensing the electrical potential information 164 includes utilization of at least one electrode. In one example, one or more electrodes are gold electrodes. In another example, one or more electrodes are silver/silver-chloride electrodes.

In one example, the method includes applying a stimulus 170 to the infant. In various examples, the method further includes storing a history of one or a combination of: the suck signal, the electrical potential information, the suck profile indication, and the applied stimulus 172. In various examples, the method further includes analyzing or displaying one or a combination of: the suck signal, the electrical potential information, the suck profile indication, and the applied stimulus to provide a real time indication of oral activity of the infant. In some examples, applying the stimulus 170 includes providing or adjusting a mechanical stimulus to the infant's face. In one example, the mechanical stimulus includes importing one or more linear displacements of approximately 600-900 microns in approximately a 10 millisecond time period to the infant's orofacial system.

The present subject matter includes a method of assembling a system. In one example, the method includes coupling an orofacial sensor, such as a suck sensor, with a processor and coupling one or more orofacial sensors, such as facial musculature sensors, with the processor. In some examples, the method further includes pneumatically coupling the suck sensor to a pacifier, such as a baglet of the pacifier. In some examples, the method further includes coupling the suck sensor to a receiver assembly. In some examples, the method further includes integrating each facial musculature sensor with an electrode.

In various embodiments, the method further includes coupling a stimulus control module with the processor. In various examples, the method further includes electrically coupling a stimulation device, such as a stimulus probe, to the stimulus control module. In some examples, the method further includes integrating the stimulation device with force-feedback capabilities. In one example, the stimulation device includes a motor, a stimulus applicator, and at least one stimulation device sensor. In some examples, the method includes mounting the plurality of orofacial sensors, the processor, and the stimulation device in a device, such as a housing, adapted to interface with orofacial tissue of the infant.

It is noted that it is preferable to sterilize all components of the system that come into contact with the infant. One way to sterilize, among many, is by the use of ethylene oxide.

The present subject matter allows for the non-invasive, objective, and rapid electrophysiologic assessment of trigeminal-facial function and suck biomechanics in infants, such as premature infants, at risk for neurological impairments and developmental disabilities. These neurological impairments and development disabilities may include pervasive developmental delays, sensory perception and integration disorders, sensorimotor dysfunction, cognitive impairments, literacy, language, and speech disorders, hemorrhage, respiratory distress syndrome, and oromotor dysfunction. By diagnosing neurological impairments and development disabilities early in an infant's life, the infant may be introduced to appropriate corrective action at an earlier time and as a result, reduce or eliminate the incidence or severity of the impairment or disability detected. Further, infants who use the system may develop higher IQs than their counterparts who were not introduced to the system.

Additionally, the present system may return information to a user regarding how well the infant's brain stem circuits and other parts of the brain are connected. The system may inform the user with information regarding how well the infant is responding when he/she is sucking, including the organization of his/her motor system, suck, duration and frequency, and muscle reflexes—all in real time on a display.

Study

Currently, studies of real time sampling of the biomechanics and electrophysiology associated with non-nutritive suck are underway for both normal term infants and clinical populations in a NICU.

The clinical populations in the NICU include infants experiencing respiratory distress syndrome, oromotor dysfunction, and brain infarcts. A total of 390 premature infants will participate in the study over a four year period concluding in the year 2007. The NICUs participating in the study include: Stormont-Vail Regional Health Center in Topeka, Kans. and Kansas University Medical Center in Kansas City, Kans.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

What is claimed is:

1. A system for use with a subject having a mouth, the system comprising:

a baglet, adapted for non-nutritive sucking on by the subject;

a plurality of orofacial sensors, adapted to sense at least one non-nutritive suck signal and at least one facial musculature signal, the plurality of orofacial sensors including a plurality of electrodes configured to sense the at least one facial musculature signal;

a processor, adapted to receive the at least one non-nutritive suck signal and the at least one facial musculature signal; and a stimulus device configured to apply a mechanical stimulus on tissue of the subject outside of the subject's mouth, the stimulus device using at least one sensor for operating the stimulus device under force-feedback, such that the stimulus device is programmed to follow movement of at least a portion of the tissue outside of the subject's mouth to impart stimulus delivery, wherein the processor is configured to automatically compute a non-nutritive suck profile indication using one or both of: the at least one non-nutritive suck signal and the at least one facial musculature signal, and to compute a suck deficiency indication using, at least in part, the non-nutritive suck profile indication and a predetermined suck profile, and the stimulus device provides the stimulus based, at least in part, on the suck deficiency indication.

2. The system as recited in claim 1, wherein the baglet comprises a baglet opening, and wherein an orofacial sensor is pneumatically coupled to the baglet opening to sense the at least one non-nutritive suck signal.

3. The system as recited in claim 2, wherein the orofacial sensor pneumatically coupled to the baglet opening is a pressure transducer.

4. The system as recited in claim 2, further comprising a receiver assembly couplable with the orofacial sensor pneumatically coupled to the baglet opening,
    wherein the receiver assembly is adapted for detachable coupling of the baglet.

5. The system as recited in claim 1, wherein plurality of electrodes include at least some electrodes spaced 4.5 millimeters apart from one another.

6. The system as recited in claim 5, wherein the plurality of electrodes are located at a baglet base to sense the at least one facial musculature signal of the subject.

7. The system as recited in claim 1, wherein the plurality of electrodes includes at least some electrodes arranged annularly at a base of the baglet and 4 millimeters in diameter.

8. The system as recited in claim 7, further comprising a stimulus control module adapted to provide a stimulus control signal to the stimulus device.

9. The system as recited in claim 1, wherein the stimulus device further comprises:
    a motor, adapted to transpose a stimulus control signal to a mechanical action; and
    a stimulus applicator mechanically coupled to the motor, the stimulus applicator adapted to impart force to the subject's orofacial system.

10. The system as recited in claim 9, wherein the motor further comprises at least one stimulation device sensor adapted to provide one or both of: a force signal and a displacement signal.

11. The system as recited in claim 1, further comprising at least one memory storage device adapted to store a history of one or a combination of: the at least one suck signal, the at least one facial musculature signal, the non-nutritive suck profile indication, the suck deficiency indication, a stimulus control signal, a force signal, and a displacement signal.

12. The system as recited in claim 1, further comprising means for analyzing and displaying, in real time, one or a combination of: the at least one suck signal, the at least one facial musculature signal, the non-nutritive suck profile indication, the suck deficiency indication, a stimulus control signal, a force signal, and a displacement signal.

13. The system of claim 1, wherein the system is configured to operate without inputs or signals from apparatus for measuring breath or breathing.

14. A system for evaluating an orofacial system of a subject having a mouth, the system comprising:
    a plurality of orofacial sensors including a plurality of electrodes configured to sense at least one facial musculature signal from the subject;
    a processor, adapted to receive each facial musculature signal; and
    a stimulation device, coupled to the processor and configured to impart a stimulus to the orofacial system of the subject adjacent to the subject's mouth, the stimulation device operated using a force-feedback configuration, such that the stimulation device is programmed to follow movement of at least a portion of the orofacial system adjacent to the subject's mouth to impart stimulus delivery,
    wherein the processor is adapted to compute a non-nutritive suck profile indication using the at least one facial musculature signal and to compute a suck deficiency indication using, at least in part, the non-nutritive suck profile indication and a predetermined suck profile.

15. The system as recited in claim 14, wherein each orofacial sensor comprises an electrode, the electrode positioned to sense the facial musculature signal of the subject.

16. The system as recited in claim 14, wherein the processor is adapted to automatically compute the non-nutritive suck deficiency indication.

17. The system as recited in claim 14, further comprising a stimulus control module adapted to provide a stimulus control signal,
    wherein the stimulus control signal is based, at least in part, on the suck deficiency indication, and
    wherein the stimulus control signal is used to adjust or initiate the stimulus provided to the subject.

18. The system as recited in claim 14, further comprising at least one memory storage device adapted to store a history of one or a combination of: the at least one facial musculature signal, the non-nutritive suck profile indication, a suck deficiency indication, and a stimulus control signal.

19. The system as recited in claim 14, further comprising a display device adapted to illustrate, in real time, one or a combination of: the at least one facial musculature signal, the non-nutritive suck profile indication, a suck deficiency indication, and a stimulus control signal.

20. The system of claim 14, wherein the system is configured to operate without inputs or signals from apparatus for measuring breath or breathing.

21. A system for evaluating an orofacial system of a subject having a mouth, the system comprising:
    a baglet, adapted for non-nutritive sucking on by the subject;
    a plurality of orofacial sensors, adapted to sense at least one non-nutritive suck signal and at least one facial musculature signal;
    a processor, adapted to receive each non-nutritive suck signal and each facial musculature signal;
    a stimulation device, coupled to the processor and adapted to impart a stimulus to the orofacial system of the subject near the subject's mouth, the stimulation device operated in a force-feedback configuration, such that the stimulation device is programmed to follow movement of at least a portion of the orofacial system adjacent to the subject's mouth to provide stimulus delivery; and
    a display device, coupled to the processor,
    wherein at least one orofacial sensor comprises a plurality of electrodes, and
    wherein the processor is adapted to compute a non-nutritive suck profile indication using one or both of: the at least one non-nutritive suck signal and the at least one facial musculature signal and to compute a suck deficiency indication using, at least in part, the non-nutritive suck profile indication and a predetermined suck profile.

22. The system as recited in claim 21, further comprising at least one memory storage device adapted to store a history of at least one of: the at least one non-nutritive suck signal, the at least one facial musculature signal, the stimulus, and the non-nutritive suck profile indication.

23. The system of claim 21, wherein the system is configured to operate without inputs or signals from apparatus for measuring breath or breathing.

24. A method comprising:
    sensing a non-nutritive suck signal from a subject;
    sensing electrical potential information of the subject's perioral musculature;

computing a non-nutritive suck profile indication using one or both of: the non-nutritive suck signal and the electrical potential information;

comparing the non-nutritive suck profile indication to a predetermined suck profile; and providing a stimulus to the subject's tissue adjacent to the subject's mouth, the stimulus based, at least in part, on comparing the non-nutritive suck profile indication to the predetermined suck profile, the stimulus applied using a force-feedback approach programmed to follow movement of at least a portion of the tissue adjacent to the subject's mouth to provide stimulus delivery.

25. The method as recited in claim 24, wherein computing the non-nutritive suck profile indication and comparing the non-nutritive suck profile indication to the predetermined suck profile is performed in real time.

26. The method as recited in claim 24, wherein sensing the non-nutritive suck signal comprises inserting a baglet into the subject's mouth.

27. The method as recited in claim 24, wherein sensing the non-nutritive suck signal comprises sensing one or a combination of: a suck intensity, a suck duration, and a suck frequency.

28. The method as recited in claim 24, further comprising storing a history of at least one of: the non-nutritive suck signal, the electrical potential information, the non-nutritive suck profile indication, and the stimulus.

29. The method as recited in claim 24, further comprising analyzing at least one of: the non-nutritive suck signal, the electrical potential information, the non-nutritive suck profile indication, and the stimulus.

30. The method as recited in claim 24, further comprising displaying at least one of: the non-nutritive suck signal, the electrical potential information, the non-nutritive suck profile indication, and the stimulus.

31. The method of claim 24, wherein the computing is done without inputs or signals from apparatus for measuring breath or breathing.

32. A method comprising:

coupling a plurality of orofacial sensors to a processor;

coupling a stimulation device to the processor, the stimulation device configured to produce a physical force on a subject's orofacial system adjacent to the subject's mouth and to operate under force-feedback, such that the stimulation device is programmed to follow movement of the subject's orofacial system adjacent to the subject's mouth to impart effective stimulus delivery; and mounting the plurality of orofacial sensors, the processor, and the stimulation device in a device adapted to interface with orofacial tissue, wherein at least one orofacial sensor is adapted to sense a non-nutritive suck signal, wherein at least one orofacial sensor is adapted to sense electrical potential information from orofacial tissue, and wherein the processor is adapted to compute a suck profile indication using one or both of: the non-nutritive suck signal and the electrical potential information, and to compute a suck deficiency indication using, at least in part, the non-nutritive suck profile indication and a predetermined suck profile.

33. The method as recited in claim 32, further comprising integrating an orofacial sensor providing the electrical potential information with an electrode.

34. The method as recited in claim 32, wherein coupling the stimulation device to the processor comprises coupling an assembly comprising a motor, a stimulus applicator, and at least one stimulation sensor to the processor.

35. The method of claim 32, wherein the processor does not use inputs or signals from apparatus for measuring breath or breathing.

* * * * *